(12) United States Patent
Lüdtke et al.

(10) Patent No.: US 6,458,078 B1
(45) Date of Patent: Oct. 1, 2002

(54) ENDOSCOPE FITTED WITH AN ELECTRIC SYSTEM AND A LIGHT GUIDE

(75) Inventors: Thorsten Lüdtke, Hamburg; Thomas Wosnitza, Lüneburg; Jens Peter Wulfsberg, Neritz; Andreas Mückner, Berlin, all of (DE)

(73) Assignee: Olympus Winter & IBE GmbH, Hamburg (DE)

( * ) Notice: Subject to any disclaimer, the term of this patent is extended or adjusted under 35 U.S.C. 154(b) by 7 days.

(21) Appl. No.: 09/678,919

(22) Filed: Oct. 4, 2000

(30) Foreign Application Priority Data

Oct. 5, 1999 (DE) .......................... 199 47 811

(51) Int. Cl.[7] ............................................... A61B 1/06
(52) U.S. Cl. ..................................... 600/178; 600/160
(58) Field of Search ........................... 600/160, 167, 600/118, 130, 103, 110, 109, 182

(56) References Cited

U.S. PATENT DOCUMENTS

| 5,166,787 A | 11/1992 | Irion |
| 5,436,553 A | 7/1995 | Pepper et al. |
| 5,594,497 A | 1/1997 | Ahern et al. |

*Primary Examiner*—Henry Bennett
*Assistant Examiner*—Sabrina Dagostino
(74) *Attorney, Agent, or Firm*—Rankin, Hill, Porter & Clark LLP

(57) ABSTRACT

A medical endoscope with sealed housing and receiving an electrically powered and/or controlled system, further comprising an installed light guide sealed against the ambience and fitted with electric/light (E/L) transducers at one end, is characterized in that a light/electricity (L/E) transducer is mounted at the other end of the light guide, one of the light guide ends being mounted inside the housing and the associated transducer being electrically connected to the electrical system.

8 Claims, 1 Drawing Sheet

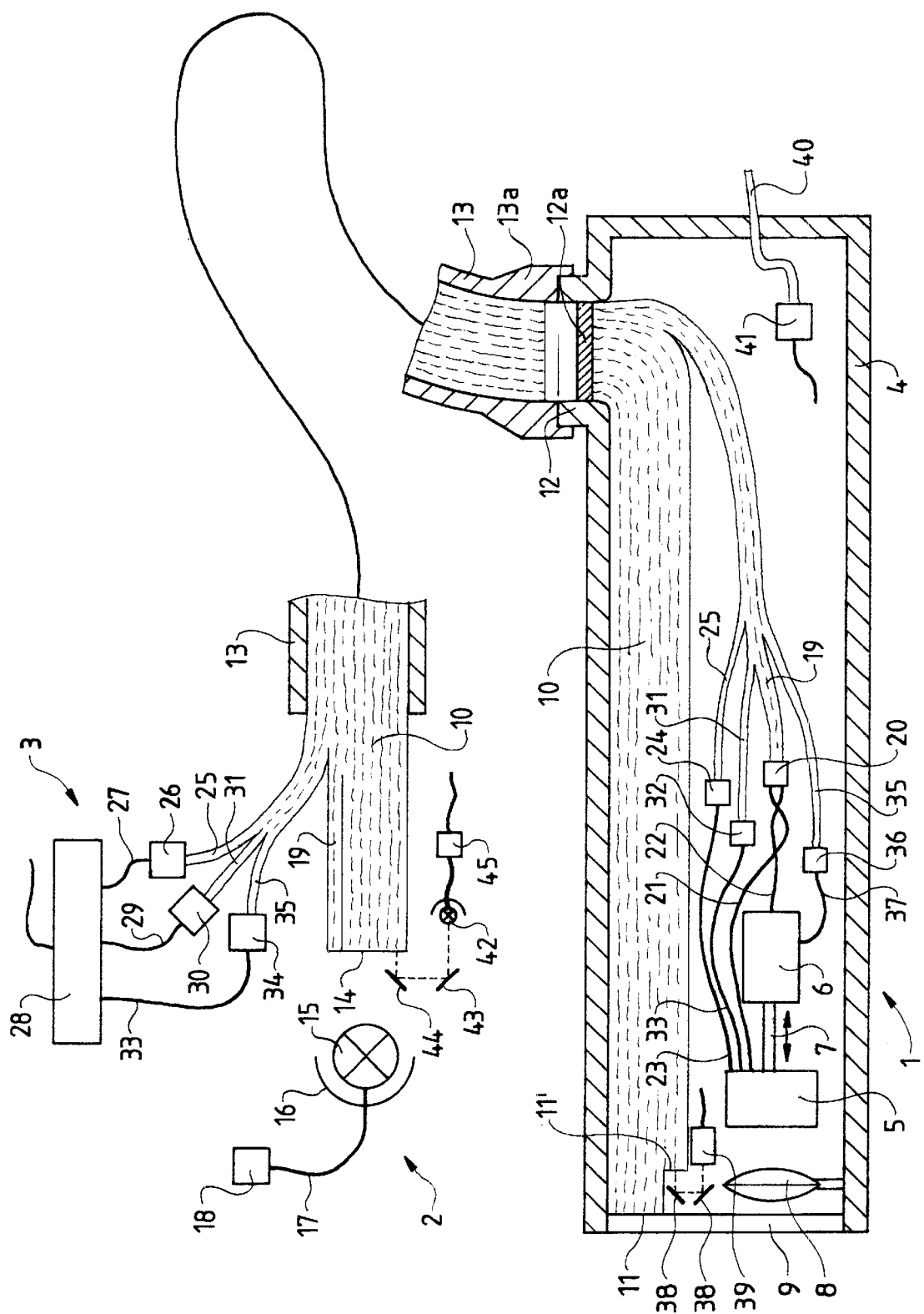

ENDOSCOPE FITTED WITH AN ELECTRIC SYSTEM AND A LIGHT GUIDE

BACKGROUND OF THE INVENTION

1. Field of the Invention

The present invention relates to an endoscope fitted with a sealed housing and an electrically powered and/or controlled system inside the housing, the endoscope including a light guide sealed against the outside and installed in the housing and fitted at one end with electricity/light transducers.

2. Description of Related Art

Endoscopes of this species are standard design today. The light guide typically is in the form of bundles of optic fibers. As a rule the light guide runs from a lateral, proximal input through the endoscope to a distal end of the endoscope. Light radiates from the light guide at the endoscope distal end surface to illuminate the field of view. A light-guide hook-up cable runs from the lateral input of the endoscope to a lamp, which illuminates the proximal end of the hook-up cable. The lamp in this instance constitutes the electricity/light (E/L) transducer.

Medical endoscopes have a sealed housing protecting the internal optical and electrical devices against exposure to liquids and vapors. Protection against vapors is required due to sterility-mandated steam-autoclaving. The sealing problems encountered in this design have been substantially solved as regards the installation of light guides. Illustratively, full sealing can be attained using soldered glass windows.

Electrical systems installed inside the endoscope, for instance video cameras, stepping motors for focusing etc., however must be powered electrically, that is, being fed with current. Accordingly, these internal electrical systems require external control lines to control their operation or to transmit signals to the outside, for instance control feedback or, in the case of a video camera, a video signal.

Aside from significantly unsatisfactory solutions such as integrated batteries constituting the power supply, or wireless signal transmission, the state of the art typically resorts to electric lines for power and for signal transmission. In addition to the already substantial sealing problems attending the light guides, additional sealing problems are introduced when using electric lines, connectors and the like. In practice, the sealing problems associated with the electric lines, connectors, etc are more difficult to overcome than those presented by the light guides.

SUMMARY OF THE INVENTION

An objective of the present invention is to create an endoscope of the above species which eliminates or reduces the sealing problems present in the prior art.

In the invention, the power supply line is a light guide fitted at one end with an E/L transducer and, at the other end, with a light/electricity (L/E) transducer. Using an electric bulb as the E/L transducer and a power L/E transducer at the other end, namely inside the endoscope housing, the electric systems in said housing is then supplied with power. Using modulated E/L transducers such as modulated electric bulbs at one end of a light guide and an L/E transducer designed for signaling purposes at the other end, a data transmission path is set up to act as a control line or as a signal transmission line for instance of the video signal. Appropriate electro-optic components are available economically and in appropriate dimensions. Electrical lines with their attendant feed through and sealing problems are avoided. The proven sealing techniques for light guides, for instance employing 100% tight windows, can be used.

Moreover, this technique offers the known advantage of reduced susceptibility to spurious electric radiation, which creates a significant problem in the vicinity of electrosurgical instruments.

The light guide used for transmission purposes may be installed in the endoscope housing separately and with its own feed through or access port. However, according to one features of the present invention, use is made of some of the cross-section of the illumination light guide. This space is already present for illumination and, using the proven sealing technique, may be retained to insert the guide into the endoscope and pass it through the endoscope.

The cross-sectional portion of the illumination light guide used as the light guide may terminate more shortly inside the endoscope for the purpose of being coupled to an L/E transducer. The illumination of the transducer may be carried out by the illuminating light source over the common, proximal cross-section. Advantageously, however, and according to another feature of the present invention, the light guide used for transmission purposes is installed over the full installation length together with the illuminating light guide. However, the light guide used for transmission purposes is apposed to the illuminating light guide and presented as a separate bundle of optic fibers that is accessible separately at both ends.

In further accordance with the present invention, the light guide can branch off the illuminating light guide at one or both ends and may advantageously run as far as the assembly site of the associated transducer.

In accordance with another feature of the present invention, the light source used for illumination in particular may serve as a high-power E/L transducer, that is, to feed current. However, the light source may also be modulated and therefore, optionally in superposition, it may be used for data transmission into the endoscope.

Alternatively, and in further accordance with the present invention, a separate light source may be used as the proximal E/L transducer. Such separate light source is of low power and in the form of an LED. This separate light source therefore serves to transmit signals very rapidly and at minimal power.

In further accordance with the present invention, a reverse signal flow is possible to communicate signals from the endoscope to the outside. Such signals may constitute, for instance, a feedback of control signals and/or transmission of video signals.

Using a plurality of transducer-equipped light guides, complex power supplies, control and data transmissions can be carried out using light guide technology. The light guides furthermore may be used for bi-directional signal transmission, optionally with additional power transmission.

BRIEF DESCRIPTION OF THE DRAWING

These and further features of the invention will be apparent with reference to the following description and drawing, which schematically shows a cross-section of an endoscope and a light source with control and receiving systems.

DETAILED DESCRIPTION OF THE PREFERRED EMBODIMENTS

The FIGURE shows an endoscope 1, an externally-mounted illuminating light source 2, and a control and receiving system 3 configured in the area of the illuminating light source 2.

The endoscope 1 is fitted with a closed housing 4 sealing against the surrounding environment. The housing receives an electric system including a video camera 5 and an electric stepping motor 6. The stepping motor 6 is provided to move an adjusting bar 7 forward/rearward within the housing 4. Movement of the adjustment bar 7 serves to adjust the video camera 5 relative to an objective lens 8, which is mounted distally from the video camera and which observes the field of view in front of the distal end through a window 9 of the endoscope 1.

A distal end zone of the endoscope 1 is occupied, except for the space taken up by the electric system 5, 6, with an illuminating light guide 10. The light guide 10 is in the form of a bundle of optic fibers. Due to sealing requirements, a distal end surface 11 of the light guide 10 terminates or ends behind the window 9. Light radiates from the light guide distal end surface 11 through the window and into the viewing field.

The illuminating light guide 10 is guided proximally into a hook-up stub 12 which, in conventional manner, projects sideways or laterally from the housing 4 of the endoscope 1. Inside the hook-up stub 12, the illuminating light guide 10 terminates in front of a window 12a illustratively soldered in place and ensuring 100% sealing of the housing. Outside the stub 12, the illuminating light guide 10 continues inside a hook-up cable with a sheath 13 which, by means of a socket 13a, is plugged in the shown manner onto the hook-up stub 12. The illuminating light guide 10 runs inside the hook-up cable as far as the illuminating light source 2 where its proximal end surface 14 is illuminated by an electric bulb 15 with reflector. The bulb 15 is powered through a conductor 17 by a power source 18.

A light guide 19 is apposed to the illuminating light guide 10 and runs from it from the proximal end surface 14 into the housing 4 of the endoscope 1. Within the endoscope housing, the light guide branches off or separates from the light guide 10, and is connected to an L/E transducer 20. The L/E transducer 20 is a power transducer, via electric conductors 21 and 22, applies current to the video camera 5 and the stepping motor 6.

A video signal from the video camera 5 is transmitted through an electric data line 23 and is coupled by an E/L transducer 24 to a light guide 25. The light guide 25, in turn, is apposed to the illuminating light guide 10 but laterally branches off or separates from the light guide 10 at the proximal end in front of the illumination source 2. The proximal end of the light guide 25 is connected to an L/E transducer 26 that is linked, by a data line 27, to a control system 28 used for control and image processing purposes.

Control signals controlling the video camera 5 are transmitted from the control system 28 through an electric line 29 to an E/L transducer 30. Light signals from the E/L transducer 30 are transmitted through a light guide 31 which, in turn, travels together with the illumination light guide 10 as far as the inside of the housing 4 of the endoscope 1. Within the housing 4, the light guide 31 branches off from the illumination light guide 10 and is connected to an L/E transducer 32. Electrical control signals from the L/E transducer are, via an electric line 33, transmitted to the video camera 5.

The electric motor 6 is controlled in a manner similar to that of the video camera. The control system 28 communicates electrical control signals through an electric line 33 to an E/L transducer 34. Light control signals are transmitted from the E/L transducer 34, via a light guide 35, to an L/E transducer 36. Electrical control signals are transmitted from the L/E transducer 36, via an electric line 37, to the electric motor 6.

In a variation of the design shown above in relation to the connection stub 12, the illumination light guide 10 also can run continuously from its distal end surface 11 to its proximal end surface 14. If, in the shown and advantageous embodiment, the light guide 10 is designed with a detachable hook-up cable, then care must be taken at the interface of the window 12a that the illumination light guide 10 and the separate transmitting light guides 19, 25, 31 and 35—which optionally also may consist of single fibers—each be supported in mutually opposite and flush manner at the interface in order to prevent cross-radiation from one light guide to another. The window 12a also may be designed in the form of a corresponding number of panes mutually separated by optical stops.

The illuminating light guide 10 also may be used for the transmission of the light to a device within the endoscope for purposes of communication or power. As shown in the Figure, it may terminate by means of a portion of the cross-section inside the housing 4 of the endoscope 1 into a distal end surface 11'. Light radiating from the distal end surface 11' is coupled by deflecting mirrors 38 onto an L/E transducer 39 implementing power supply to an electric apparatus (not shown).

Moreover, a light guide 40 may be used to implement a transmission path into or out of the endoscope. The light guide 40 is installed separately from the illuminating light guide 10 and passes in a sealed manner through the housing 4. A distal end of the light guide 40 is connected to a transducer 41 inside the housing 4.

In addition to being illuminated by the electric bulb 15 at its proximal end surface 14, a portion of the illuminating light guide 10 may be illuminated by a bulb 42 by means of deflecting mirrors 43 and 44. The bulb 42 is powered by a power source 45, for instance with modulated light. This modulated light for instance can be transmitted from the transducer 39 inside the endoscope housing 4 at the offset surface 11' and be used to control an electric device (not shows). The path between the transducer 39 inside the housing 4 and the additional bulb 42 at the proximal end of the illuminating light guide also may be used in a reverse manner to transmit data from inside the endoscope to the outside.

What is claimed is:

1. A medical endoscope (1) fitted with a sealed housing (4) and an electrical system (5, 6) inside said housing (4), said endoscope further comprising a sealed light guide (10, 19, 25, 31, 35, 40) that is installed in the housing (4) and provided at a first end with a electricity/light (E/L) transducer (15, 24, 30, 34, 42), wherein a light/electricity (L/E) transducer (20, 26, 32, 36, 39) is disposed at a second end of the light guide, and one of said first and second light guide ends being mounted inside the housing (4) wherein the transducer (20, 24, 32, 36, 39, 41) at said one of said first and second light guide ends is electrically connected to the electrical system (5, 6).

2. The endoscope as claimed in claim 1, wherein the light guide (11', 19, 25, 31, 35) is designed as a cross-sectional portion of an illuminating light guide (10), a proximal end of said illuminating light guide being illuminated by a light source (15) and said illuminating light guide being used to illuminate the viewing field.

3. The endoscope as claimed in claim 2, wherein, after manufacture, the cross-sectional portion of the illuminating light guide (10), which is designed as a bundle of optic fibers, is apposed to said light guide (10) in the form of a bundle of optic fibers (19, 25, 31, 35).

4. The endoscope as claimed in claim 2, wherein at least one end of the light guide (19, 25, 31, 35) branches off a corresponding end of the illuminating light guide (10) and extends toward the transducer (26, 30, 34, 24, 32, 20, 36).

5. The endoscope as claimed in claim 2, wherein the light source (15) illuminating the illuminating light guide (10) constitutes the E/L transducer.

6. The endoscope as claimed in claim 2, wherein the E/L transducer (30, 34, 42) proximally is connected separately from the light source (15) to the light guide (31, 35, 10).

7. The endoscope as claimed in claim 1, wherein the E/L transducer (24) is connected to a distal end of the light guide (25) and the L/E transducer (26) is connected to a proximal end of the light guide (25).

8. The endoscope as claimed in claim 1, wherein the housing (4) receives ends of further light guides (19, 25, 31, 35, 40) fitted with transducers (15, 20, 24, 26, 30, 32, 34, 36, 41).

* * * * *